US009417136B2

(12) United States Patent
Son et al.

(10) Patent No.: US 9,417,136 B2
(45) Date of Patent: Aug. 16, 2016

(54) METHOD FOR CALCULATING A THERMAL PROTECTION FACTOR

(75) Inventors: Eui Dong Son, Yongin-si (KR); Hyeon Chung Kim, Yongin-si (KR); Ji Hyun Kim, Yongin-si (KR); Hyun Jung Choi, Yongin-si (KR); Gae Won Nam, Yongin-si (KR); Tae Ryong Lee, Yongin-si (KR); Jin Ho Chung, Seoul (KR); Seon Pil Jin, Seoul (KR)

(73) Assignees: AMOREPACIFIC CORPORATION (KR); SNU R&DB FOUNDATION (KR)

( * ) Notice: Subject to any disclaimer, the term of this patent is extended or adjusted under 35 U.S.C. 154(b) by 440 days.

(21) Appl. No.: 14/000,543

(22) PCT Filed: Feb. 15, 2012

(86) PCT No.: PCT/KR2012/001145
§ 371 (c)(1),
(2), (4) Date: Aug. 20, 2013

(87) PCT Pub. No.: WO2012/118284
PCT Pub. Date: Sep. 7, 2012

(65) Prior Publication Data
US 2013/0329766 A1    Dec. 12, 2013

(30) Foreign Application Priority Data
Feb. 28, 2011  (KR) .................. 10-2011-0017894

(51) Int. Cl.
*G01N 25/00*    (2006.01)
*G01K 11/00*    (2006.01)
(Continued)

(52) U.S. Cl.
CPC . *G01K 11/00* (2013.01); *A61B 5/01* (2013.01); *A61B 5/441* (2013.01)

(58) Field of Classification Search
USPC ............................ 374/45, 120, 121, 110, 141
See application file for complete search history.

(56) References Cited

U.S. PATENT DOCUMENTS

| 6,309,631 | B1 | 10/2001 | Cooper et al. |
| 2009/0196321 | A1* | 8/2009 | Spaulding ................ A61K 8/27 374/45 |

(Continued)

FOREIGN PATENT DOCUMENTS

| GB | 2352174 | 1/2001 |
| JP | 2005162695 A | 6/2005 |

(Continued)

OTHER PUBLICATIONS

Written Opinion for International Application No. PCT/KR2012/001145 dated Sep. 20, 2012.
(Continued)

*Primary Examiner* — Mirellys Jagan
(74) *Attorney, Agent, or Firm* — Cantor Colburn LLP

(57) ABSTRACT

The present invention relates to a method for calculating a thermal protection factor, wherein the method comprises the steps of: applying heat to a first area coated with a thermal protection material, and a second area not coated with the thermal protection material; measuring the respective saturation temperatures of the first area and second area; calculating a first energy by dividing the energy corresponding to the heat applied to the first area by the saturation temperature of the first area; calculating a second energy by dividing the energy corresponding to the heat applied to the second area by the saturation temperature of the second area; and calculating the thermal protection factor of a thermal protection material by dividing the first energy by the second energy or dividing the difference between the first energy and the second energy by the first energy.

8 Claims, 5 Drawing Sheets

(51) Int. Cl.
*A61B 5/01* (2006.01)
*A61B 5/00* (2006.01)

(56) References Cited

U.S. PATENT DOCUMENTS

| | | | | |
|---|---|---|---|---|
| 2012/0014015 A1* | 1/2012 | Anderson | ............... | G11B 5/012 360/73.03 |
| 2012/0121521 A1* | 5/2012 | Bulluck | ................ | A61K 8/042 424/59 |

FOREIGN PATENT DOCUMENTS

| | | |
|---|---|---|
| KR | 1020060109648 A | 10/2006 |
| KR | 1020100055433 A | 5/2010 |
| KR | 1020110010553 A | 2/2011 |
| WO | 2011010798 | 1/2011 |
| WO | 2011065877 | 6/2011 |
| WO | 2011136849 | 11/2011 |

OTHER PUBLICATIONS

International Search Report with English Translation for International Application No. PCT/KR2012/001145 dated Sep. 20, 2012.
Chinese Office Action—CN Application No. CN201280018647.6 dated Dec. 3, 2014, citing U.S. Pat. No. 6,309,631 and WO2011010798.
European Office Action—EP Application No. 12752148.2 dated Jul. 25, 2014, citing GB2352174, WO2011010798, WO2011136849 and WO2011065877.

* cited by examiner

METHOD FOR CALCULATING A THERMAL PROTECTION FACTOR

TECHNICAL FIELD

Embodiments relate to a method for generating a thermal protection factor.

BACKGROUND ART

Being the largest organ, the human skin acts as a barrier that protects the body against many harmful factors such as temperature, moisture, ultraviolet (UV) light, etc. from external environment. The skin may be aged or damaged due to various factors. In particular, it is known that heat accelerates skin aging by increasing the temperature of the skin, triggering various inflammatory responses and degrading collagen in the dermis by inducing increase of collagenases.

In order to avoid or prevent skin damage caused by heat, a standard for evaluating the ability of preventing thermal skin aging is required. Although sun protection factor (SPF) is available as an index for the ability of protecting from UV, a material which provides protection from UV may not provide protection from heat, and vice versa. Therefore, a standard for evaluating the ability of preventing thermal skin damage is needed.

DISCLOSURE

Technical Problem

An aspect of the present disclosure is directed to providing a method for generating a thermal protection factor that allows objective evaluation of thermal protection effect of a material.

Technical Solution

According to an embodiment, a method for generating a thermal protection factor may include: applying heat to a first area coated with a thermal protection material and to a second area not coated with the thermal protection material; measuring a saturation temperature of the first area; measuring a saturation temperature of the second area; calculating a first energy by dividing the energy corresponding to the heat applied to the first area by the saturation temperature of the first area; calculating a second energy by dividing the energy corresponding to the heat applied to the second area by the saturation temperature of the second area; and calculating a thermal protection factor of the thermal protection material using the first energy and the second energy.

In an embodiment, said calculating the thermal protection factor may comprise calculating the thermal protection factor by dividing the first energy by the second energy.

In another embodiment, said calculating the thermal protection factor may comprise calculating the thermal protection factor by dividing the difference between the first energy and the second energy by the first energy.

Advantageous Effects

By providing a thermal protection factor as an objective index of thermal protection effect apart from the sun protection factor (SPF), an aspect of the present disclosure allows objective evaluation of the effect of a cosmetic product including a thermal protection material.

MODE FOR INVENTION

Hereinafter, the present disclosure will be described in detail through examples while referring to the attached drawings. However, the present disclosure is not limited by the following examples.

Figure 1:
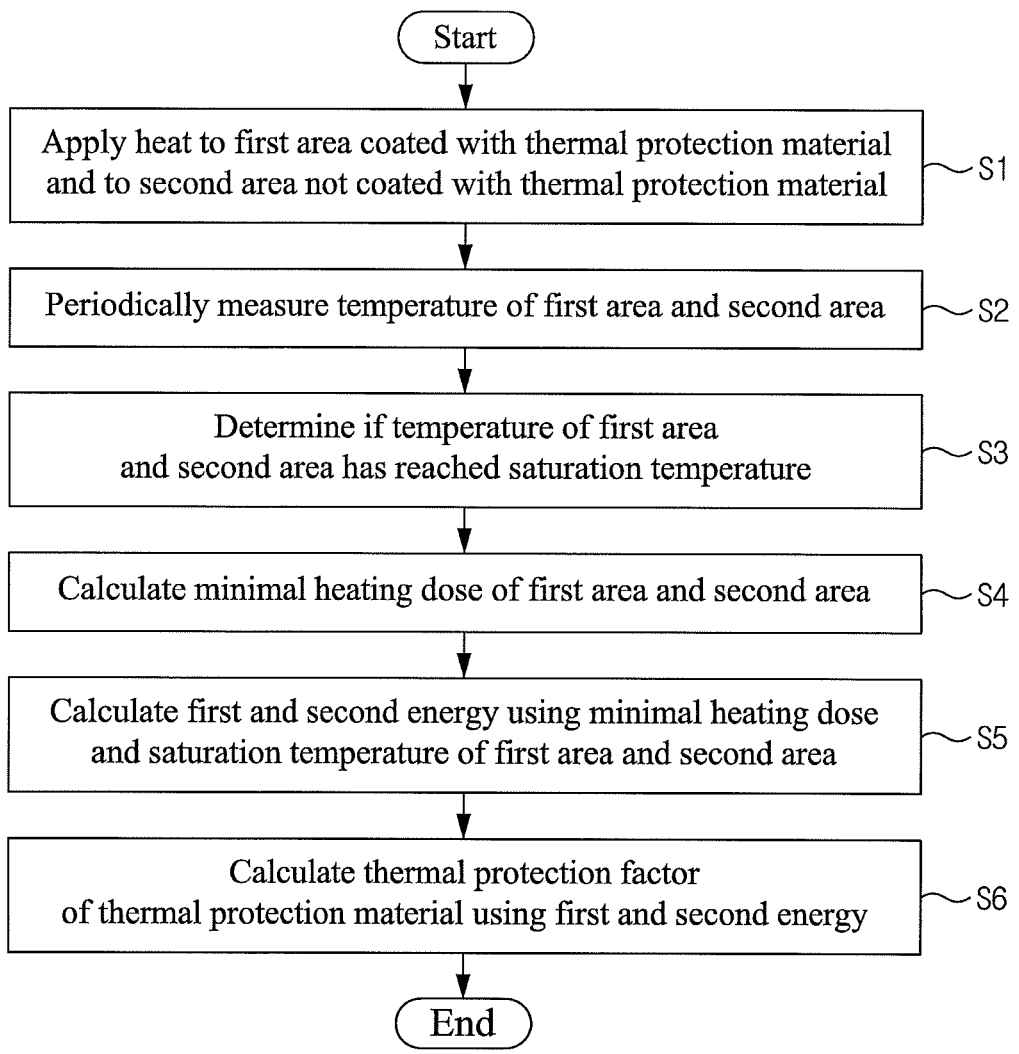
FIG. 1 is a flow chart of a method for generating a thermal protection factor according to an embodiment.

FIG. 1 is a flow chart of a method for generating a thermal protection factor according to an embodiment.

Referring to FIG. 1, heat may be applied to a first area coated with a thermal protection material and to a second area not coated with the thermal protection material (S1). The first area is an area where the thermal protection material for which a thermal protection factor is to be generated is coated. For example, the first area may be an area of skin to which a cosmetic product including a thermal protection material is applied. The second area is an area where the thermal protection material is not coated as a control. For example, the second area may be an area of naked skin where no material is applied.

In an embodiment, heat may be applied to the first area and to the second area by exposing them to infrared (IR) light. However, application of heat to the first area and to the second area is not limited to infrared radiation and heat may be applied to the first area and to the second area through different methods or means not described herein.

Figure 2:
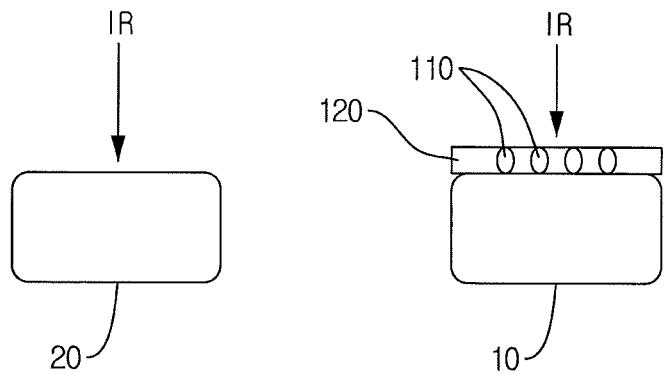
FIG. 2 is a schematic diagram of an experimental apparatus for generating a thermal protection factor according to an embodiment.

FIG. 2 is a schematic diagram of an experimental apparatus for generating a thermal protection factor according to an embodiment.

Referring to FIG. 2, a first area 10 and a second area 20 may be heated by irradiating infrared light to the first area 10 and the second area 20. The first area 10 may be coated with an infrared absorbing material 110 included in a vehicle material 120 as a thermal protection material. Meanwhile, the second area 20 may not be coated with the infrared absorbing material 110. Referring to FIG. 2, nothing is coated on the second area 20. However, in another embodiment, only the vehicle material 120 excluding the infrared absorbing material 110 or another adequate material that can act as a control material may be coated on the second area 20.

Referring again to FIG. 1, the temperature of the first area and the second area may be measured periodically while applying heat to the first area and second area (S2). For example, the temperature of the first area and the second area may be measured with 30-second intervals, although not being limited thereto. The measurement of the first area and the second area may be carried out using a non-contact type infrared (IR) thermometer, a needle type thermometer or another adequate temperature measuring means.

Figure 3A:
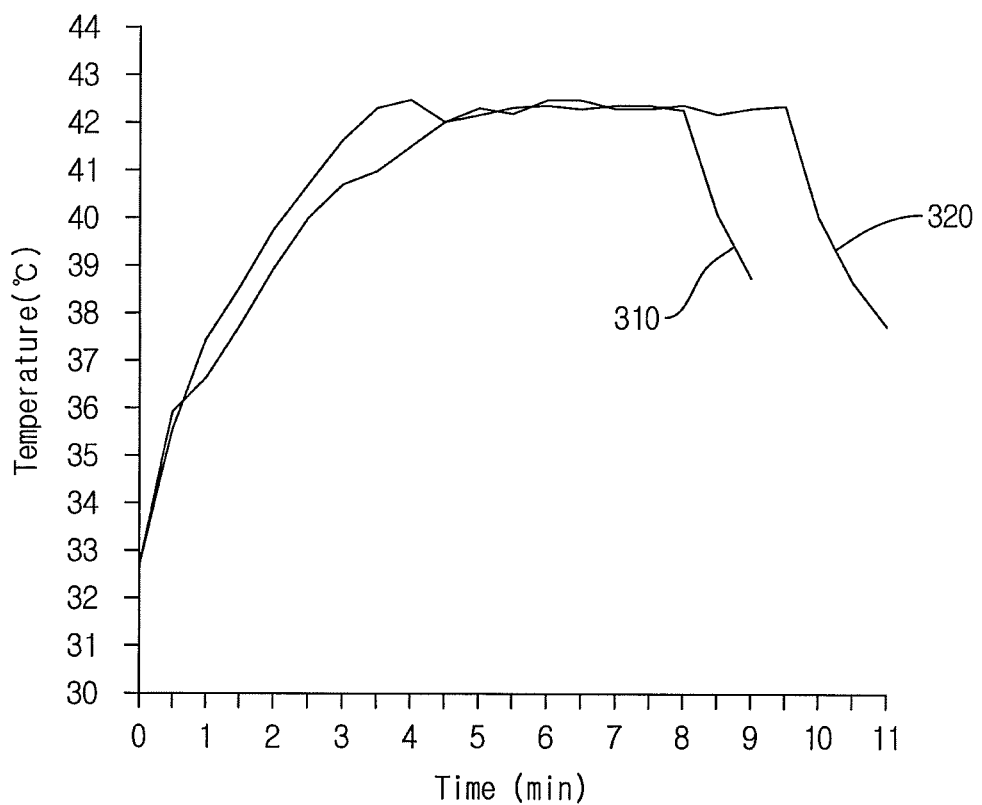
FIGS. 3a and 3b show a result of measuring subcutaneous temperature using different thermometers.
Figure 3B:
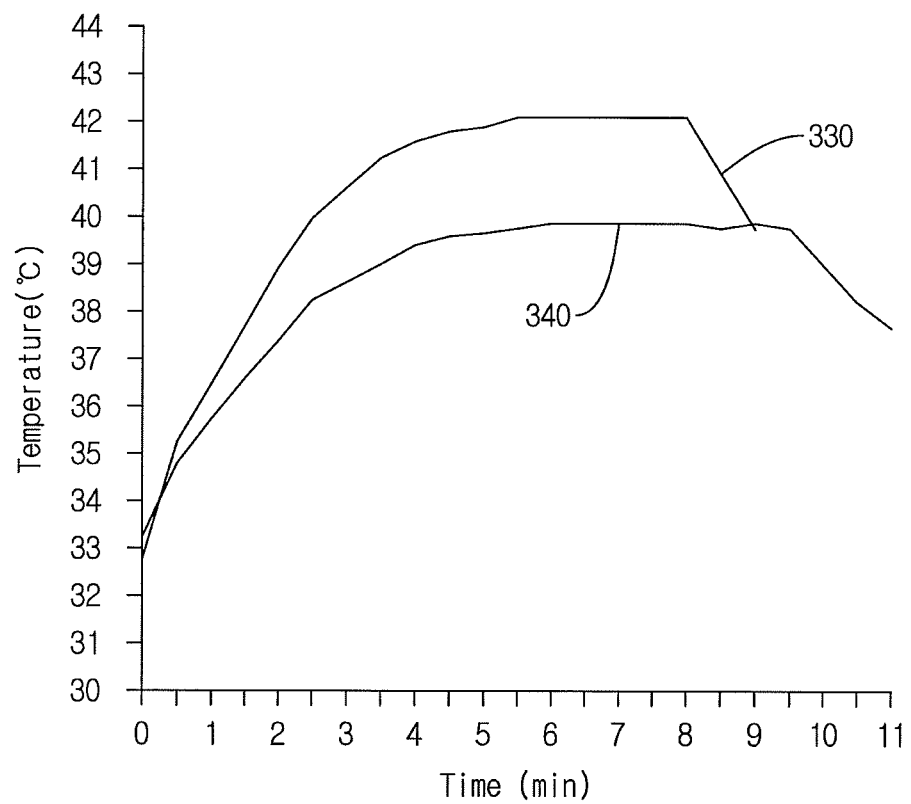

FIG. 3a shows a result of measuring subcutaneous temperature using an infrared thermometer and FIG. 3b shows a result of measuring subcutaneous temperature using a needle type thermometer. Referring to FIGS. 3a and 3b, the graphs 310, 330 represent the subcutaneous temperature of the skin area where only a vehicle not including a thermal protection material is applied with infrared radiation time. And, the graphs 320, 340 represent the subcutaneous temperature of the skin area where urea is included in a solvent at a concentration of about 3.5% as a thermal protection material with infrared radiation time. However, the method for generating a thermal protection factor according to the present disclosure is not limited by the temperature measuring method or means described herein.

Then, the saturation temperature of the first area and the second area may be calculated from the measured temperature of the first area and the second area (S3). The temperature of the heated skin does not rise any more if it reaches a certain temperature. This temperature is referred to as saturation temperature. For example, after measuring the temperature of the first area and the second area at regular time intervals, if the measured temperature does not rise any more for a predetermined number of measurement times, the highest temperature among the temperatures measured until then may be determined as the saturation temperature.

Table 1 shows an example of measuring subcutaneous temperatures measured at 30-second intervals.

TABLE 1

| | Measurement number | | | | | | | |
|---|---|---|---|---|---|---|---|---|
| | 1 | 2 | 3 | 4 | 5 | 6 | 7 | 8 |
| Temperature (° C.) | 39.8 | 40.2 | 41 | 40.7 | 40.5 | 40.6 | 40.3 | 40.2 |

For example, if the temperature does not rise any more for 4 or more measurements, the highest temperature until then may be determined as the saturation temperature. Referring to Table 1, the temperature at the third measurement is highest at 41° C. and the temperatures for the 4 measurements from the fourth to seventh measurement is lower than 41° C. Accordingly, the temperature 41° C. at the third measurement may be determined as the saturation temperature.

In another embodiment, if the measured temperature does not rise any more for a predetermined number of measurements, the highest temperature until then may be determined as the saturation temperature. However, if the difference between the highest temperature and the temperature at the time point immediately preceding the time point at which the highest temperature is measured is smaller than a predetermined threshold value, the temperature measured at the immediately preceding time point may be determined as the saturation temperature.

Table 2 shows another example of measuring subcutaneous temperatures measured at 30-second intervals.

TABLE 2

| | Measurement number | | | | | | |
|---|---|---|---|---|---|---|---|
| | 1 | 2 | 3 | 4 | 5 | 6 | 7 |
| Temperature (° C.) | 39.8 | 40.2 | 40.5 | 40.3 | 40.4 | 40.2 | 40.1 |

For example, if the temperature does not rise any more for 4 or more measurements, the highest temperature until then may be determined as the saturation temperature. However, if the difference between the highest temperature and the temperature at the time point immediately preceding the time point at which the highest temperature is measured is smaller than a predetermined threshold value, the temperature measured at the immediately preceding time point from the time point at which the highest temperature is measured may be determined as the saturation temperature. The threshold value may be determined adequately considering, for example, the error range of the temperature measuring means. For example, assuming that the temperature is measured around 40° C. and the error range of the thermometer is about 1%, the threshold value may be determined as 0.4° C. Referring to Table 2, the temperature at the third measurement is 40.5° C. and the temperatures for the 4 measurements from the fourth to seventh measurement is lower than 40.5° C. The temperature 40.5° C. at the third measurement is the highest, but the difference between the temperature of the third measurement and the temperature of the second measurement is 0.3° C., which is smaller than the threshold value 0.4° C. Accordingly, the temperature of the second measurement 40.2° C. may be determined as the saturation temperature.

Then, the minimal heating dose (MHD) of the first area and the second area may be calculated based on the saturation temperature of the first area and the second area (S4). As used herein, the minimal heating dose refers to the total energy corresponding to the heat applied to the first area and the second area until the temperature reaches the saturation temperature. In an embodiment, the minimal heating dose may be calculated based on the energy applied per unit area. For example, the minimal heating dose may be expressed with the unit $J/cm^2$.

Figure 4:
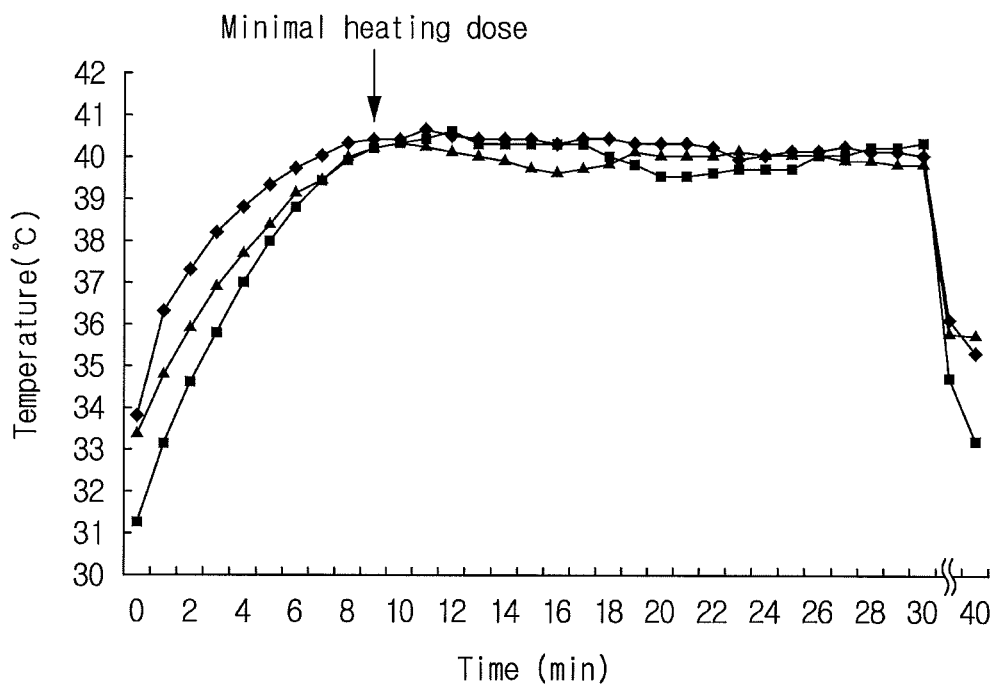
FIG. 4 shows a result of measuring subcutaneous temperature to calculate minimal heating dose (MHD).

FIG. 4 shows a result of measuring subcutaneous temperature to calculate minimal heating dose. Referring to the measurement data shown in FIG. 4, the temperature does not rise any more after about 10 minutes of infrared radiation. Accordingly, the temperature at about 10 minutes corresponds to the saturation temperature. The data of FIG. 4 were obtained by applying heat to skin using an infrared light source. The output of the infrared light source was about 2.02 $W/cm^2$. Accordingly, the minimal heating dose determined from the measurement data is about 1212 $J/cm^2$, corresponding to the output of the light source multiplied by 600 seconds.

Referring again to FIG. 1, first energy and second energy may be calculated based on the minimal heating dose and the saturation temperature of the first area and the second area (S5). As used herein, the first and second energy refers respectively to the energy required to raise the surface temperature of the first area and the second area by 1° C. until the first area and the second area reach the saturation temperature. The first energy may be calculated by dividing the minimal heating dose of the first area calculated in S4 by the saturation temperature of the first area. Likewise, the second energy may be calculated by dividing the minimal heating dose of the second area by the saturation temperature of the second area.

Then, a thermal protection factor of the thermal protection material coated on the first area may be calculated using the first energy and the second energy (S6). In an embodiment, the thermal protection factor of the thermal protection material may be calculated as a ratio of the first energy to the second energy. In the present disclosure, this thermal protection factor is called thermal protection factor-1 (TPF-1). That is to say, the TPF-1 of the thermal protection material is calculated by Equation 1.

$$TPF - 1 = \frac{(MHD_1)/(\Delta t_1)}{(MHD_2)/(\Delta t_2)} \qquad \text{[Equation 1]}$$

In Equation 1, $MHD_1$ is the minimal heating dose of the first area and $MHD_2$ is the minimal heating dose of the second area. Further, $\Delta t_1$ is the saturation temperature of the first area and $\Delta t_2$ is the saturation temperature of second area. That is to say, the numerator of the right side of Equation 1 corresponds to the first energy and the denominator corresponds to the second energy.

For example, assuming that about 150 mJ/cm² of energy per unit area is required to raise the temperature of a first area to which a cosmetic product including a thermal protection material is applied by 1° C., and about 50 mJ/cm² of energy per unit area is required to raise the temperature of a second area to which the cosmetic product is not applied by 1° C., the TPF-1 of the cosmetic product is 3. This means that, as a result of using the cosmetic product, the energy required to raise the skin temperature by 1° C. is increased to about 3 times. Accordingly, the thermal protection effect of the cosmetic product can be objectively evaluated by calculating the TPF-1. By using a product with high TPF-1, skin aging caused by heat can be reduced or prevented.

Figure 5:
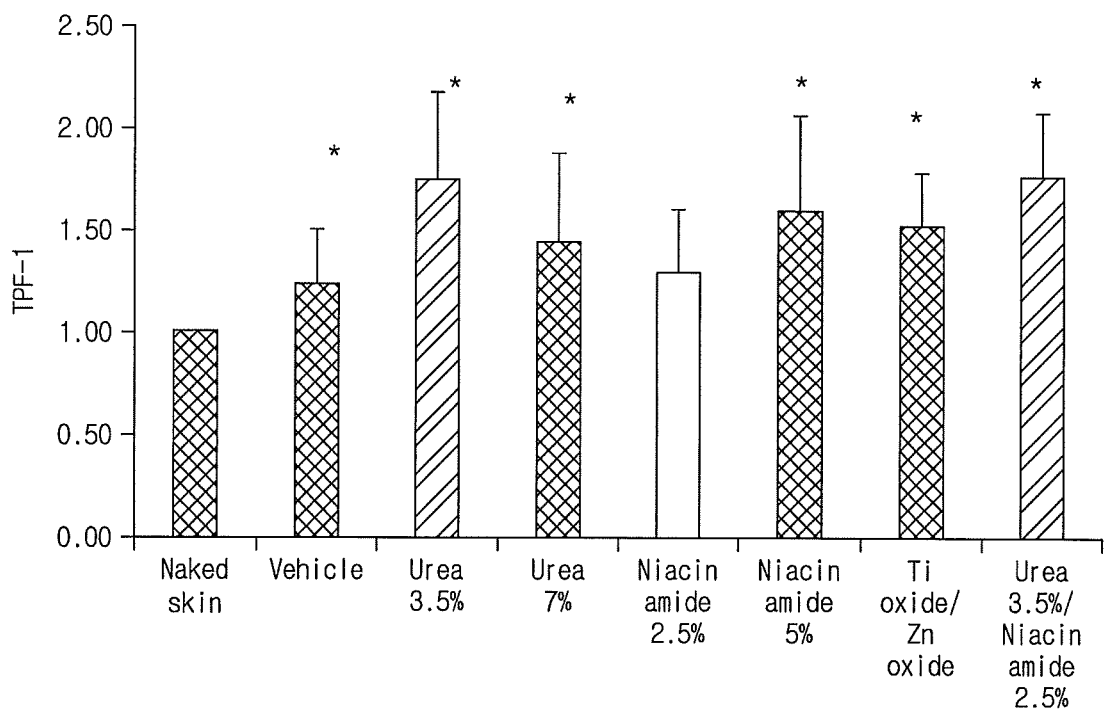
FIG. 5 shows thermal protection factor-1 (TPF-1) of different materials generated according to an embodiment.

Table 3 shows TPF-1 of different materials and FIG. 5 shows the TPF-1 as a graph. The TPF-1 shown in Table 3 and FIG. 5 was obtained from the naked skin area with nothing applied as the second area and the skin area to which a vehicle, 3.5% urea, 7% urea, 2.5% niacinamide, 5% niacinamide, a mixture of titanium (Ti) oxide and zinc (Zn) oxide or a mixture of 3.5% urea and 2.5% niacinamide is applied as the first area. The percentage (%) of urea or niacinamide represents the mass percentage of the urea or niacinamide in a mixture of the urea or niacinamide with a vehicle material.

The thermal protection factor TPF-1 represents the thermal protection effect of a material as compared to that of a control. In another embodiment, the thermal protection effect may be represented as the ratio of shielded energy. A thermal protection factor calculated in this regard is referred to as thermal protection factor-2 (TPF-2). That is to say, the TPF-2 of a thermal protection material may be calculated by Equation 2.

$$TPF - 2 = \frac{\left(\frac{MHD_1}{\Delta t_1}\right) - \left(\frac{MHD_2}{\Delta t_2}\right)}{\left(\frac{MHD_1}{\Delta t_1}\right)} \times 100 \qquad \text{[Equation 2]}$$

For example, assuming that about 150 mJ/cm² of energy per unit area is required to raise the temperature of a first area to which a cosmetic product including a thermal protection material is applied by 1° C., and about 50 mJ/cm² of energy per unit area is required to raise the temperature of a second area to which the cosmetic product is not applied by 1° C., it can be said that about 100 mJ/cm² of energy per unit area is shielded by the thermal protection material. In this case, the heat shielding ratio or TPF-2 of the thermal protection material is 100/150 or about 67% in percentage. Accordingly, by calculating the TPF-2, the ratio of thermal energy shielded by a material can be objectively evaluated.

Figure 6:
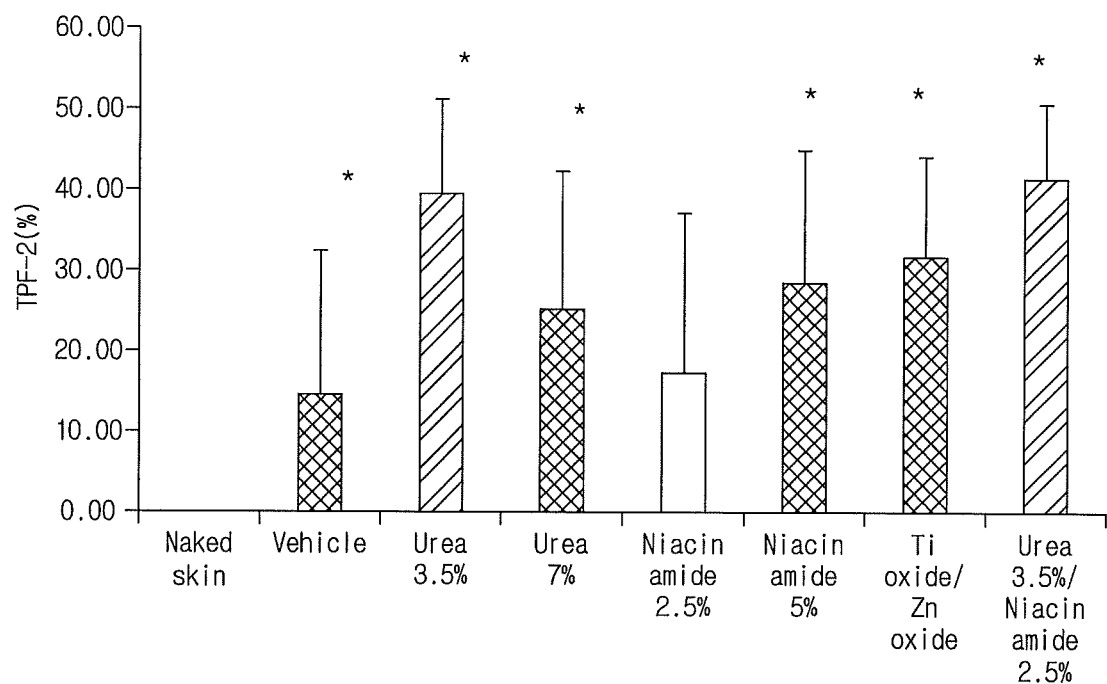
FIG. 6 shows thermal protection factor-2 (TPF-2) of different materials generated according to another embodiment.

Table 4 shows TPF-2 of different materials and FIG. 6 shows the TPF-2 as a graph. The TPF-2 shown in Table 4 and FIG. 6 was obtained from the naked skin area with nothing applied as the second area and the skin area to which a vehicle, 3.5% urea, 7% urea, 2.5% niacinamide, 5% niacinamide, a mixture of titanium (Ti) oxide and zinc (Zn) oxide or a mixture of 3.5% urea and 2.5% niacinamide is applied as the first area.

TABLE 3

|  | Vehicle | 3.5% urea | 7% urea | 2.5% niacinamide | 5% niacinamide | Ti oxide/ Zn oxide | 3.5% urea/ 2.5% niacinamide |
| --- | --- | --- | --- | --- | --- | --- | --- |
| 1 | 1.61 | 2.46 | 2.34 | 1.98 | 2.32 | 1.63 | 2.54 |
| 2 | 1.65 | 2.62 | 2.17 | 1.46 | 1.43 | 1.75 | 1.98 |
| 3 | 0.92 | 1.64 | 1.04 | 0.82 | 1.04 | 1.29 | 1.73 |
| 4 | 1.05 | 1.35 | 1.35 | 1.33 | 1.39 | 1.75 | 1.69 |
| 5 | 1.3 | 1.61 | 1.26 | 1.16 | 1.42 | 1.99 | 1.47 |
| 6 | 1.32 | 1.5 | 1.15 | 1.15 | 2.35 | 1.46 | 1.49 |
| 7 | 1.02 | 1.42 | 1.2 | 1.28 | 1.25 | 1.32 | 1.86 |
| 8 | 1.47 | 1.68 | 1.38 | 1.11 | 1.98 | 1.33 | 1.48 |
| 9 | 0.95 | 1.49 | 1.24 | 1 | 1.08 | 1.09 | 1.71 |
| 10 | 1.01 | 1.65 | 1.21 | 1.54 | 1.61 | 1.53 | 1.6 |
| Mean | 1.23 | 1.74 | 1.43 | 1.28 | 1.59 | 1.51 | 1.76 |
| Standard deviation | 0.28 | 0.44 | 0.44 | 0.32 | 0.48 | 0.27 | 0.32 |

TABLE 4

|   | Vehicle | 3.5% urea | 7% urea | 2.5% niacinamide | 5% niacinamide | Ti oxide/ Zn oxide | 3.5% urea/ 2.5% niacinamide |
|---|---|---|---|---|---|---|---|
| 1 | 38 | 59 | 57 | 49 | 57 | 39 | 61 |
| 2 | 38 | 61 | 53 | 30 | 29 | 42 | 49 |
| 3 | −10 | 38 | 3 | −23 | 3 | 22 | 42 |
| 4 | 4 | 26 | 26 | 25 | 28 | 43 | 41 |
| 5 | 23 | 38 | 21 | 14 | 29 | 50 | 32 |
| 6 | 23 | 32 | 11 | 11 | 24 | 30 | 31 |
| 7 | 2 | 29 | 16 | 22 | 20 | 24 | 46 |
| 8 | 30 | 39 | 26 | 8 | 48 | 23 | 31 |
| 9 | −5 | 33 | 20 | 0 | 7 | 8 | 42 |
| 10 | 1 | 39 | 17 | 35 | 38 | 34 | 38 |
| Mean | 14.40 | 39.40 | 25.00 | 17.10 | 28.30 | 31.50 | 41.30 |
| Standard deviation | 18.01 | 11.73 | 17.24 | 20.06 | 16.63 | 12.56 | 9.31 |

The above embodiments of the method for generating a thermal protection factor were described above with reference to the flowchart shown in FIG. 1. While the method was described as a series of blocks for simplicity of explanation, the present disclosure is not limited by the order of the blocks, as some blocks may occur in different orders and/or concurrently with other blocks from that shown and described herein. It can be appreciated that various other branches, flow paths and orders of the blocks may be implemented which achieve the same or similar result. Moreover, some blocks may be optional in implementing the method of the present disclosure.

Further, while the exemplary embodiments have been shown and described, it will be understood by those skilled in the art that various changes in form and details may be made thereto without departing from the spirit and scope of this disclosure as defined by the appended claims. Therefore, it is intended that this disclosure not be limited to the particular exemplary embodiments disclosed as the best mode contemplated for carrying out this disclosure, but that this disclosure will include all embodiments falling within the scope of the appended claims.

INDUSTRIAL APPLICABILITY

Embodiments relate to a method for generating a thermal protection factor.

The invention claimed is:

1. A method for generating a thermal protection factor, comprising:
   applying heat to a first area coated with a thermal protection material and to a second area not coated with the thermal protection material;
   measuring a saturation temperature of the first area;
   measuring a saturation temperature of the second area;
   calculating a first energy by dividing energy corresponding to heat applied to the first area by the saturation temperature of the first area;
   calculating a second energy by dividing energy corresponding to heat applied to the second area by the saturation temperature of the second area; and
   calculating a thermal protection factor of the thermal protection material using the first energy and the second energy.

2. The method for generating a thermal protection factor according to claim 1, wherein said calculating the thermal protection factor comprises calculating the thermal protection factor by dividing the first energy by the second energy.

3. The method for generating a thermal protection factor according to claim 1, wherein said calculating the thermal protection factor comprises calculating the thermal protection factor by dividing the difference between the first energy and the second energy by the first energy.

4. The method for generating a thermal protection factor according to claim 1, wherein said measuring the saturation temperature of the first area comprises:
   measuring the temperature of the first area at a plurality of time points; and
   for a predetermined number of time points, if the temperature measured at each time point is the same as or lower than the temperature measured at an immediately preceding time point, determining the highest temperature among the temperatures measured at the time points as the saturation temperature of the first area.

5. The method for generating a thermal protection factor according to claim 1, wherein said measuring the saturation temperature of the first area comprises:
   measuring the temperature of the first area at a plurality of time points;
   for a predetermined number of time points, if the temperature measured at each time point is the same as or lower than the temperature measured at an immediately preceding time point, comparing the highest temperature among the temperatures measured at the time points with the temperature at a time point immediately preceding the time point at which the highest temperature is measured;
   if the difference between the highest temperature and the temperature at the time point immediately preceding the time point at which the highest temperature is measured is equal to or greater than a predetermined threshold value, determining the highest temperature as the saturation temperature of the first area; and
   if the difference between the highest temperature and the temperature at the time point immediately preceding the time point at which the highest temperature is measured is smaller than the threshold value, determining the temperature at the time point immediately preceding the time point at which the highest temperature is measured as the saturation temperature of the first area.

6. The method for generating a thermal protection factor according to claim 1, wherein said measuring the saturation temperature of the second area comprises:
   measuring the temperature of the second area at a plurality of time points; and
   for a predetermined number of time points, if the temperature measured at each time point is the same as or lower than the temperature measured at an immediately preceding time point, determining the highest temperature among the temperatures measured at the time points as the saturation temperature of the second area.

7. The method for generating a thermal protection factor according to claim 1, wherein said measuring the saturation temperature of the second area comprises:

measuring the temperature of the second area at a plurality of time points;

for a predetermined number of time points, if the temperature measured at each time point is the same as or lower than the temperature measured at an immediately preceding time point, comparing the highest temperature among the temperatures measured at the time points with the temperature at a time point immediately preceding the time point at which the highest temperature is measured;

if the difference between the highest temperature and the temperature at the time point immediately preceding the time point at which the highest temperature is measured is equal to or greater than a predetermined threshold value, determining the highest temperature as the saturation temperature of the second area; and if the difference between the highest temperature and the temperature at the time point immediately preceding the time point at which the highest temperature is measured is smaller than the threshold value, determining the temperature at the time point immediately preceding the time point at which the highest temperature is measured as the saturation temperature of the second area.

8. The method for generating a thermal protection factor according to claim 1, wherein said applying heat comprises applying infrared light to the first area and to the second area.

* * * * *